United States Patent [19]
Wu

[11] Patent Number: 6,162,794
[45] Date of Patent: Dec. 19, 2000

[54] ERYTHROMYCIN DERIVATIVES

[75] Inventor: Yong-Jin Wu, East Lyme, Conn.

[73] Assignee: Pfizer Inc., New York, N.Y.

[21] Appl. No.: 09/355,092

[22] PCT Filed: May 1, 1998

[86] PCT No.: PCT/IB98/00661

§ 371 Date: Jul. 20, 1999

§ 102(e) Date: Jul. 20, 1999

[87] PCT Pub. No.: WO98/51696

PCT Pub. Date: Nov. 19, 1998

Related U.S. Application Data

[60] Provisional application No. 60/046,150, May 9, 1997.

[51] Int. Cl.[7] ............................ A61K 31/70; C07H 17/08
[52] U.S. Cl. ................................. 514/29; 536/7.2; 536/7.5
[58] Field of Search .......................... 536/7.2, 7.5; 514/29

[56] References Cited

U.S. PATENT DOCUMENTS 5,631,355  5/1997  Asaka et al. ............................. 536/7.5

*Primary Examiner*—Elli Peselev
*Attorney, Agent, or Firm*—Peter C. Richardson; Paul H. Ginsburg; Jolene W. Appleman

[57] ABSTRACT

The invention relates to compounds of the formula:

and to pharmaceutically acceptable salts thereof, wherein R and Z are as defined herein.

The invention also relates to pharmaceutical compositions containing the compounds of formula I, methods of using said compounds of formula I in the treatment of infections and methods of preparing said compounds of formula I.

12 Claims, No Drawings

ERYTHROMYCIN DERIVATIVES

This application is a 371 of PCT/IB98/00661 filed May 1, 1998 and also claims benefit of Provisional No. 60/046,150 filed May 9, 1997.

BACKGROUND OF THE INVENTION

This invention relates to novel 11-amino-9-deoxo-11-deoxy-9-imino-5-O-desosaminyl-6-O-methyl-3-oxoerythronolide A, 9N,11N-dihydropyrazole, 11,12-carbamate and 9,11-diamino-9-deoxo-11-deoxy-5-O-desosaminyl-6-O-methyl-3-oxoerythronolide A, 9N,11N-tetrahydropyrazole, 11,12-carbamate derivatives. The compounds of this invention are useful as antibiotic agents in mammals, including man, as well as in fish and birds. The compounds of the present invention are broad-spectrum macrolide antibiotics that are effective against infections caused by certain gram-positive and gram-negative bacteria as well as protozoa.

Macrolide antibiotics are known to be useful in the treatment of a broad spectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. patent application Ser. No. 60/063676, filed Oct. 29, 1997 (Yong-Jin Wu), U.S. application Ser. No. 60/063161, filed Oct. 29, 1997 (Yong-Jin Wu), U.S. application Ser. No. 60/054866, filed Aug. 6, 1997 (Hiroko Masamune, Yong-Jin Wu, Takushi Kaneko and Paul R. McGuirk), all of which are incorporated herein by reference in their entirety. Like azithromycin and other macrolide antibiotics, the novel macrolide compounds of the present invention possess potent activity against various bacterial infections and protozoa infections as described below.

SUMMARY OF THE INVENTION

The present invention relates to compounds of the formula:

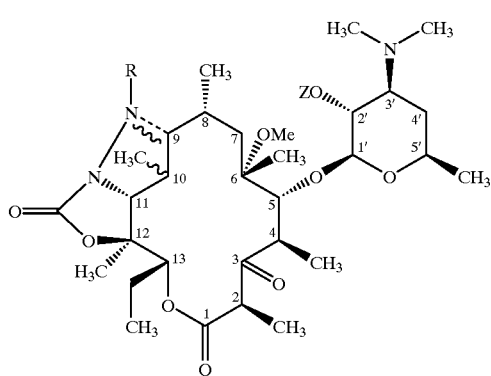

and to pharmaceutically acceptable salts thereof, wherein:
R is H, $R^1$, $C(=O) R^1$, $C(=O) OR^1$, $(CH_2)_m R^3$, or is absent, wherein m is an integer from 0 to 6;
$R^3$ is a 5–10 membered heterocycyl or $C_6–C_{10}$ aryl, wherein said heterocycyl and aryl groups are optionally substituted by 1 to 3 substituents independently selected from the group consisting of —C(O)OR$^4$, —OR$^4$, $C_1–C_6$ alkanoyl, halo, nitro, cyano, $C_1–C_6$ alkyl, —NR$^4$R$^5$, —S($C_1–C_6$ alkyl), —SO($C_1–C_6$ alkyl), —SO$_2$($C_1–C_6$ alkyl) and —SO$_2$NR$^4$R$^5$, each $R^4$ and $R^5$ is independently selected from H and $C_1–C_{10}$ alkyl, saturated or unsaturated, wherein one or two carbons of said alkyl are optionally replaced by a heteroatom selected from O, S and N, $R_1$ is selected from $C_1–C_{10}$ alkyl, saturated or unsaturated, wherein one or two carbons of said alkyl are optionally replaced by a heteroatom selected from O, S and N, and are optionally substituted by 1 to 3 substituents selected from the group consisting of —C(O)OR$^4$, —OR$^4$, $C_1–C_6$ alkanoyl, halo, nitro, cyano, $C_1–C_6$ alkyl, 5–10 membered heterocycyl, $C_6–C_{10}$ aryl, —NR$^4$R$^5$, —S($C_1–C_6$ alkyl), —SO ($C_1–C_6$ alkyl), —SO$_2$($C_1–C_6$ alkyl) and —SO$_2$NR$^4$R$^5$; and Z is H, $C(=O)R^4$ or $C(=O)R^3$, wherein $R^4$ is defined as above.

The dashed line connected to C-9 represents an optional bond that may optionally exist when R is absent.

More specific embodiments of this invention include compounds of formula I wherein R is H.

More specific embodiments of this invention include compounds of formula I wherein Z is H.

Other more specific embodiments of this invention include compounds of formula I wherein $R^1$ is absent and the dashed line connected to C-9 represents an additional bond.

Other more specific embodiments of this invention include compounds of formula I wherein R is $(CH_2)_m R^3$, where m is an integer ranging from 0 to 6 and $R^3$ is 5–10 membered heterocyclyl or $C_6–C_{10}$ aryl. Specific embodiments of $R^3$ include quinolin-4-yl, 4-phenyl-imidazol-1-yl, imidazo(4,5-b)pyridin-3-yl, 4-pyridin-3-yl-imidazol-1-yl and pyridin-3-yl.

Examples of preferred compounds of this invention include:

11-Amino-9-deoxo-11-deoxy-5-O-desosaminyl-9-imino-6-O-methyl-3-oxoerythronolide A, 9N,11N-dihydropyrazole, 11,12-carbamate;

9,11-Diamino-9-deoxo-11-deoxy-5-O-desosaminyl-6-O-methyl-3-oxoerythronolide A, 9N, 11N-tetradropyrazole, 11,12-carbamate;

9,11-Diamino-9-Deoxo-11-deoxy-5-O-desosaminyl-6-O-methyyl-3-oxo-9N-((3-quinolin-4-yl)-propyl)erythronolide A, 9N,11N-tetrahydropyrazole, 11,12-carbamate;

9,11-Diamino-9-deoxo-11-deoxy-5O-desosaminyl-6-O-methyl-3-oxo-9N-(phenylpropyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-pyridin-3-yl-thiazol-4-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-phenyl-imidazol-1-yl)-propyl) erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-pyridin-3-yl-imidazol-1-yl)-propyl)erythronolide A, 9N,11N-tetrahydropyrazole, 11,12-carbamate;

9,11-Diamino-9-dexo-11-deoxy-5-O-desosaminyl-6-O-methyl-3-oxo-9N-(3-(imidazo(4,5-b)pyridin-3-yl)- propyl)erythronolide A, 9N,11N-tetrahydropyrazole, 11,12-carbamate;

9,11-Diamino-9-11-deoxy-5-O-desosaminyl-6-O-methyl-3-oxo-9N-(3-(pyridin-3-yl)-propyl)erythronolide A, 9N,11N-tetrahydropyrazole, 11,12-carbamate;

9,11-Diamino-9-deoxo-11-deoxy-5-O-desosaminyl-6-O=methyl-3-oxo-9N-(3-(2-phenyl-thiazol-5-yl)-propyl)erythronolide A, 9N,11N-tetrahydropyrazole, 11,12-carbamate;

9,11-Diamino-9-deoxo-11-deoxy-5-O-desasaminyl-6-O-methyl-3-oxo-9N-(3-(4-phenyl-1H-imidazol-2-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-quinolin-4-yl)-propionyl)erythronolide erythronolide A, 9N,11N-tetrahydropyrazole, 11,12-carbamate;

9,11-Diamino-9-deoxo-11-deoxy-5-O-desosaminyl-6-O-methyl-3-oxo-9N-((phenyl)-propionyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-pyridin-3-yl-thiazol-4-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N(3-(4-phenyl-imidazol-1-yl)-propionyl)erythronolide A, 9N,11N-tetrahydropyrazole, 11,12-carbamate;

9,11-Diamino-9-deoxo-11-deoxy-5-O-desosaminyl-6-O=methyl-3-oxo-9N-(3-(2-phenyl-thiazol-5-yl)-propionyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-phenyl-1H-imidazol-2-yl)-propionyl)erythronolide A, 9N,11N-tetrahydropyrazole, 11,12-carbamate; and the pharmaceutically acceptable salts of said compounds.

The invention also relates to a pharmaceutical composition for the treatment of a bacterial infection or a protozoa infection in a mammal, fish, or bird which comprises a therapeutically effective amount of a compounds of formula I, or a pharmaceutically acceptable salt thereof and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula I or a pharmaceutically acceptable salt thereof.

The term "treatment", as used herein, unless otherwise indicated, includes the treatment or prevention of a bacterial infection or protozoa infection as provided in the method of the present invention.

As used herein, unless otherwise indicated, the term "bacterial infection(s)" or "protozoa infection" includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by Streptococcus pneumoniae, Haemophilus influenzae, Moraxella catarrhalis, Staphylococcus aureus, or Peptostreptococcus spp.; pharyngitis, rheumatic fever, and glomerulonephritis related to infection by Streptococcus pyogenes, Groups C and G streptococci, Clostridium diphtheriae, or Actinobacillus haemolyticum; respiratory tract infections related to infection by Mycoplasma pneumoniae, Legionella pneumophila, Streptococcus pneumoniae, Haemophilus influenzae, or Chlamydia pneumoniae; uncomplicates kin and soft tissue infections abscesses and osteomyelitis, and puerperal fever related to infection by Staphylococcus aureus, coagulase-positive staphylococci (i.e., S. epidermidis, S. hemolyticus, etc.), Streptococcus pyogenes, Streptococcus agalactiae, Streptococcal groups C-F (minute-colony streptococci), viridans streptococci, Corynebacterium minutissimum, Clostridium spp., or Bartonella henselae; uncomplicated acute urinary tract infections related to infection by Staphylococcus saprophyticus or Enterococcus spp.; urethritis and cervicitis; and sexually transmitted diseases related to infection by Chlamydia trachomatis, Haemophilus ducreyi, Treponema pallidum, Ureaplasma urealyticum, or Neiserria gonorrheae; toxin diseases related to infection by S. aureus (food poisoning and Toxic shock syndrome), or Groups A, B, and C streptococci; ulcers related to infection by Helicobacter pylori; systemic febrile syndromes related to infection by Borrelia recurrentis; Lyme disease related to infection by Borrelia burgdorferi; conjunctivitis, keratitis, and dacrocystitis related to infection by Chlamydia trachomatis, Neisseria gonorrhoeae, S. aureus, S. pneumoniae, S. pyogenes, H. influenzae, or Listeria spp.; disseminated Mycobacterium avium complex (MAC) disease related to infection by Mycobacterium avium, or Mycobacterium intracellulare; gastroenteritis related to infection by Campylobacter jejuni; intestinal protozoa related to infection by Cryptosporidium spp.; odontogenic infection related to infection by viridans streptococci; persistent cough related to infection by Bordetella pertussis; gas gangrene related to infection by Clostridium perfringens or Bacteroides spp.; and atherosclerosis related to infection by Helicobacter pylori or Chlamydia pneumoniae. Bacterial infections and protozoa infections and disorders related to such infections that may be treated or prevented in animals include the following: bovine respiratory disease related to infection by P. haem., P. multocida, Mycoplasma bovis, or Bordetella spp.; cow enteric disease related to infection by E. coli or protozoa (i.e., coccidia, cryptosporidia, etc.); dairy cow mastitis related to infection by Staph. aureus, Strep. uberis, Strep. agalactiae, Strep. dysgalactiae, Klebsiella spp., Corynebacterium, or Enterococcus spp.; swine respiratory disease related to infection by A. pleuro., P. multocida, or Mycoplasma spp.; swine enteric disease related to infection by E. coli, Lawsonia intracellularis, Salmonella, or Serpulina hyodyisinteriae; cow footrot related to infection by Fusobacterium spp.; cow metritis related to infection by E. coli; cow hairy warts related to infection by Fusobacterium necrophorum or Bacteroides nodosus; cow pink-eye related to infection by Moraxella bovis; cow premature abortion related to infection by protozoa (i.e. neosporium), urinary tract infection in dogs and cats related to infection by E. coli; skin and soft tissue infections in dogs and cats related to infection by Staph. epidermidis, Staph. intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The invention also relates to A method of preparing a compound of the formula:

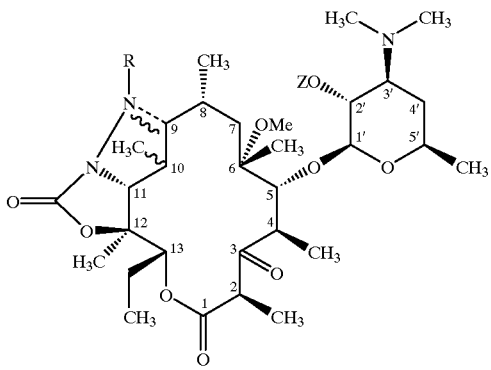

and pharmaceutically acceptable salts thereof, wherein
R is H, $R^1$, C(=O) $R^1$, C(=O) $OR^1$, $(CH_2)_mR^3$, or is absent, wherein m is an integer from 0 to 6;
$R^3$ is a 5–10 membered heterocycyl or $C_6$–$C_{10}$ aryl, wherein said heterocycyl and aryl groups are optionally substituted by 1 to 3 substituents independently selected from the group consisting of —C(O)$OR^4$, —$OR^4$, $C_1$–$C_6$ alkanoyl, halo, nitro, cyano, $C_1$–$C_6$ alkyl, —$NR^4R^5$, —S($C_1$–$C_6$ alkyl), —SO($C_1$–$C_6$ alkyl), —$SO_2$($C_1$–$C_6$ alkyl) and —$SO_2NR^4R^5$;
each $R^4$ and $R^5$ is independently selected from H and $C_1$–$C_{10}$ alkyl, saturated or unsaturated, wherein one or two carbons of said alkyl are optionally replaced by a heteroatom selected from O, S and N;
$R^1$ is selected from $C_1$–$C_{10}$ alkyl, saturated or unsaturated, wherein one or two carbons of said alkyl are optionally replaced by a heteroatom selected from O, S and N, and are optionally substituted by 1 to 3 substituents selected from the group consisting of —C(O)$OR^4$, —$OR^4$, $C_1$–$C_6$ alkanoyl, halo, nitro, cyano, $C_1$–$C_6$ alkyl, 5–10 membered heterocycyl, $C_6$–$C_{10}$ aryl, —$NR^4R^5$, —S($C_1$–$C_6$ alkyl), —SO($C_1$–$C_6$ alkyl), —$SO_2$($C_1$–$C_6$ alkyl) and —$SO_2NR^4R^5$; and
Z is H or C(=O)$R^4$, wherein $R^4$ is defined as above, which comprises treating a compound of the formula:

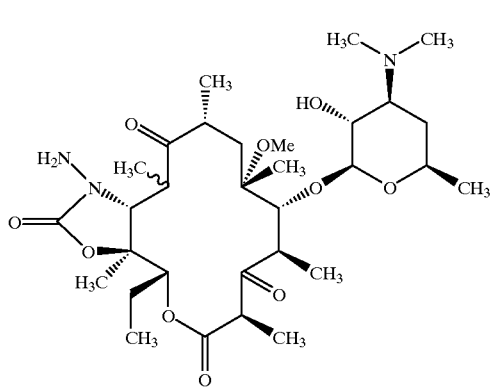

with an acid in the presence of a protic solvent to form the compound of formula I.
Preferably, said catalyst is p-toluenesulfonic acid (PTSA) or pyridinium p-toluene-sulfonate (PPTS), and said solvent is methanol, ethanol, or isopropyl alcohol.

Patients that can be treated with the compounds of formula I, and the pharmaceutically acceptable salts thereof, include mammals (in particular humans), fish, and birds suffering from infections caused by various microorganisms including Gram+ and Gram− bacteria.

In the chemical structures depicted herein, a wavy line indicates that the stereochemistry at the chiral center to which the wavy line is connected is either an R or S configuration where the wavy line is connected to a carbon atom. In the compound of formula I, the wavy line connected to C-9 of the macrolide ring indicates the chiral center C-9 is either an R or S configuration when the bond between C-9 and the N to which it is bonded is a single bond, and the wavy line connected to C-10 of the macrolide ring indicates the chiral center C-10 is either an R or S configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "5–10 membered heterocyclyl", as used herein, unless otherwise indicated, includes aromatic and non-aromatic heterocyclic groups containing one or more heteroatoms each selected from O, S and N, wherein each heterocyclic group has from 5–10 atoms in its ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that from non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluensulfonate and pamoate [i.e., 1,1'-methylene-bis-(2-hydroxy-3-naphthoate)] salts.

Those compounds of the formula I that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula I, and pharmaceutically accptable salts thereof, wherein the radiolabel is selected from $^3$H, $^{11}$C and $^{14}$C. Such radiolabelled compounds are useful as research or diagnostic tools.

Certain compounds of formula I may have asymmetric centers and therefore exist in different enantiomeric forms. This invention relates to the use of all optical isomers and stereoisomers of the compounds of formula I and mixtures thereof. In particular, the invention includes both the R and S configurations of C-9. The compounds of formulas I may also exist as tautomers. this invention relates to the use of all such tautomers and mixtures thereof.

DETAILED DESCRIPTION OF THE INVENTION the preparation of the compounds of the present invention is illustrated in the following Schemes 1 to 3.

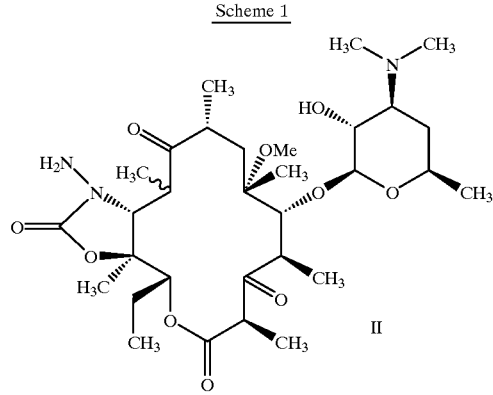

Scheme 1

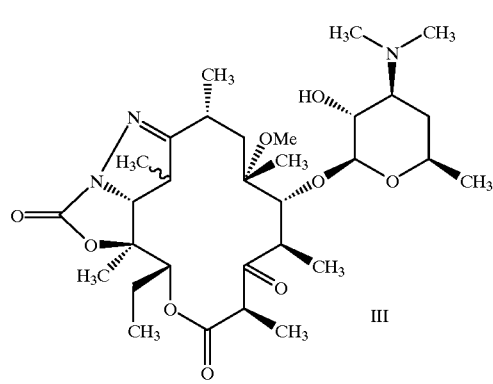

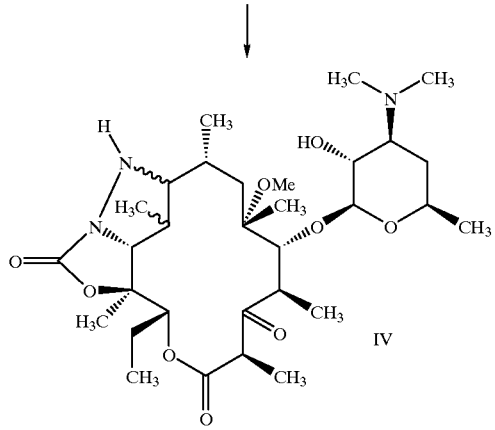

Scheme 2

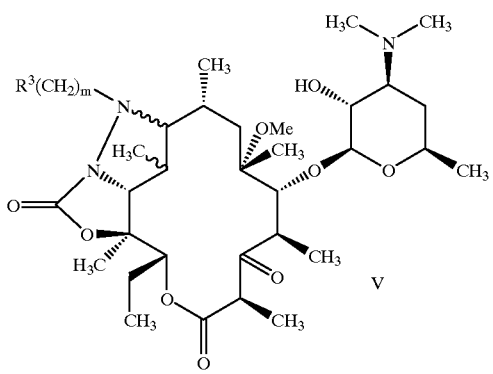

Scheme 3

In the above Schemes, "Me" indicates a methyl group. Scheme 1 illustrates the general synthesis of the compounds of the present invention wherein the C-9 of the macrolide ring is bonded to N with a double bond (formula III). In Scheme 1, the starting compound of formula II can be prepared as described in European Patent Application 676 409, published Oc. 11, 1995 and G. Griesgraber et al., "3-Keto-11,12-carbazate Derivatives of 6-Methylerythromycin A." Journal of Antibiotics, 49(5), 465–477 (1996). Scheme 2 illustrates the general synthesis of the compounds of the present invention wherein the C-9 of the macrolide ring is bonded to N with a single bond (formula IV). The compounds of formula IV can be prepared from the compounds of formula III as described in Example II. Scheme 3 illustrates another general synthesis of the compounds of the present invention wherein the C-9 of the macrolide ring is bonded to N with a single bond (formula V). The compound of formula V can be prepared from the compounds of formula IV as described in Example III. In general, the compounds of formula II can be prepared as described in European Patent Application EP 676 409, referred to above, United Kingdom patent application number 2,288,1745 (published Oct. 11, 1995), and G. Griesgraber et al., "3-Keto-11,12-carbazate Derivatives of 6-O-

Methylerythromycin A," Journal of antibiotics, 49(50, 465–477 (1996).

In Scheme 1, compounds of the formula I, wherein R is absent, the dashed line connected to C-9 represents another bond, and Z is H, can be prepared by treating a compound of the formula II with an acid such as p-toluenesulfonic acid (PTSA), or pyridinium p-toluenesulfonate (PPTS) in a protic solvent such as isopropyl alcohol, methanol or ethanol at at temperature within the range of about 50° C. to 90° C. for a period of about 4 hours to two days.

Scheme 2 illustrates a method of preparing compounds of the formula I wherein the C-9 of the macrolide ring is bonded to N with a single bond and R and Z are present as hydrogens. In Scheme 2, the compound of formula IV can be prepared by treating the compound of formula III with an acid such HOAc and a reducing agent such as $NaBH_3CN$ in a protic solvent such as methanol for about 50 hours.

Scheme 3 illustrates an additional method of preparing compounds of the formula I wherein R is of the formula $R^3(CH_2)_m$ and Z is H, wherein m is an integer from 1 to 6 and $R^3$ is defined above.

In Scheme 3, the compound of formula V can be prepared by treating the compound of formula IV with a compound of the formula $R^3(CH_2)_{m-1}$ CHO, wherein m is an integer from 1 to 6 and $R^3$ is defined as above, such as 3-(4-quinolinyl) propionaldehyde or phenylpropionaldehyde with an acid such as HOAC and a reducing agent such as $NaB(OAc)_3H$ in a solvent such as $Cl(CH_2)_2Cl$ at room temperature for about 24 hours.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts may be prepared by confentional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the maceolide-susceptible parent strain and the maceolide-resistant strain derived from it are available to provide a more accurate assessment of the compound's ability to circumvent the resistance mechanism. Strains that contain the gene with the designation of ermA/ermB/ermC are resistance to maceolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection of Erythromycin-Resistant Determinants By PCR", Antimicrobial Agents and Chemotherapy, 40(11), 2562–2566 (1996). the assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
|---|---|
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | ermB |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Streptococcus pneumoniae 0085 | susceptible |
| Haemophilus influenzae 0131 | susceptible |
| Moraxella catarrhalis 0040 | susceptible |
| Moraxella catarrhalis 1055 | erythromycin intermediate resistance |
| Escherichia coli 0266 | susceptible |

Assay II is utilized to test for activity against Pasteurella multocida and Assay III is utilized to test for activity against Pasteurella Haemolytica.

Assay II

This assay is based on the liquid dilution method in microliter format. A single colony of P. multocida (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using unioculated BHI broth. The concentrations of the test compound used range from 200 μg/mlo to 0.098 μg/ml by two-fold serial dilutions. the P. multocida inoculated BHI is diluted with uninoculated BHI broth to make a $10^4$ cell suspension per 200 μl. The BHI cell suspensions are mixed with respective serial dilutions of the test compound, and incubated at 37° C. for 18 hours. the minimum inhibitory concentration (MIC) is equal to the concentration of the compound exhibiting 100% inhibition of growth of P. multocida as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown P. haemolytica preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated P. haemolytica culture reaches 0.5 McFarland standard density, about 5 μl of the P. haemolytica culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of P. haemolytica as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (P. multocide strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The P. multocida model monitoring continues for 96 hours (four days) post challenge.

The $PD_{50}$ is a calculated dose at which the compound tested protects 50% of a group of mice from fortality due to the bacterial infection which would be lethal in the absence of drug treatment.

The compounds of formula I, and the pharmaceutically acceptable salts thereof (hereinafter "the active compounds"), may be administered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms. i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or filters, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

EXAMPLE 1

11-Amino-9-deoxo-11-deoxy-5-O-desosaminyl-6-O-methyl-9-imino-3-oxoerythronolide A 9N,11-dihydropyrazole, 11,12-carbamate (Formula I wherein R is absent, the dashed line Connected to C-9 Represents Another Bond, and Z is H)

To a solution of 11-amino-11-deoxy-5-O-desosaminyl-11-hydrazo-6-O-methyl-3-oxoerythronolide A, 11,12-carbamate (1.0 g., 1.56 mmol) in isopropyl alcohol i-PrOH (15 mL) was added PTSA.$H_2O$ (684 mg, 3.6 mmol) and the resulting solution was heated at 80° C. for 5 hours. The reaction mixture was removed from heat and poured slowly into sataturated $NaHCO_3$ (30 mL) at 0° C. i-PrOH was removed in vacuo and the residue was extracted with $CH_2Cl_2$ (3×35 mL). The combined organics were washed with $H_2O$ (40 mL) and brine (50 mL), dried over anhydrous $Na_2SO_4$, and concentrated in vacuo. The crude product was purified by preparative TLC (12×0.50 mm plates) eluting with 10% MeOH-1%, $NH_3.H_2O$-89% $CH_2Cl_2$ to afford the title compound as a pale yellow solid (399 mg, 41%) and the recovered starting material (194 mg, 19%).

$^1$H NMR (400 MHz, $CDCl_3$) δ: 5.12 (1H, dd, J=3.6, 10.4 Hz), 4.25 (1H, d, J=7.2 Hz). 4.21 (1H, d, J=9.2 Hz), 3.69 (1H, q, J=7.2 Hz), 3.64 (1H, d, J=6.8 Hz), 3.51 (1H, double sextet, J=1.2, 5.6 Hz), 3.20 (1H, dd, J=7.2, 10.0 Hz), 3.02 (2H, m), 2.69 (1H, m), 2.71 (3H, s), 2.55 (1H, m), 2.32 (6H, s), 2.02–1.51 (m), 1.48 (3H, s), 1.47 (3H, d, J=6.4 Hz), 1.32 (3h, s), 1.31 (3H, d, J=7.2 Hz), 1.22 (3H, d, J=6.0 Hz), 1.19 (3H, d, J=7.6 Hz), 1.11 (3H, d, J=7.6 Hz), and 0.90 (3H, t, J=7.2 Hz).

$^{13}$C NMR (100 MHz, $CDCl_3$) δ (attached H's): 203.61 (0), 179.87 (0), 169.30 (0), 149.16 (0), 104.03 (1), 82.86 (0), 80.63 (1), 80.25 (1), 78.54 (0), 70.28 (1), 69.52 (1), 67.04 (1), 65.69 (1), 50.40, 41,62, 40.61, 40.12, 30.85, 27.96, 22.12, 22.07, 21.05, 20.15, 19.00, 16.28, 14.37, 12.29, and 9.91.

MS:m/z 610 (M+H).

EXAMPLE 2

9,11-diamino-9-deoxo-11-deoxy-5-O-desosaminyl-6-O-methyl-3-oxoerythronolide A, 9N,11N-tetrahydropyrazole, 11,12-carbamate (formula I wherein R is H and Z is H)

To a solution of 11-amino-9-deoxo-11-deoxy-5-O-desosaminyl-9-imino-6-O-methyl-3-oxoerythronolide A, 9N,11N-dihydropyrazole, 11,12-carbamate (95 mg, 0.16 mmol) in methanol (MeOH) (1.0 mL) at room temperature was added acetic acid (HOAc) (0.14 mL, 2.45 mmol) and $NaBH_3CN$ (166 mg, 2.64 mmol) and the resulting suspension was stirred at room temperature for 17 h. HOAc (0.14 mL. 2.45 mmol) and $NaBH_3CN$ (166 mg, 2.64 mmol) were added and the reaction mixture was stirred for another 50 h. Sat. $NaHCO_3$ was added and MeOH was removed in vacuo. The aqueous layer was extracted with $CH_2Cl_2$(X3). The combined organic layers were washed with brine, dried over anhydrous $Na_2SO_4$, and concentrated in vacuo. The crude product was purified by preparative TLC (8% MeOH-1% $NH_3.H_2O$-91% $CH_2Cl_2$) to afford the title compound as a white solid (34 mg, 35%) and the recovered starting material (25 mg, 25%).

$^1$H NMR (400 MHz, $CDCl_3$) δ: 5.12 (1H, dd, J=2.8, 9.2 Hz), 4.60 (1H, d, J=5.6 Hz), 4.40 (1H, d, J=7.2 Hz), 4.33 (1H, d, J=4.0 Hz), 4.83 (1H, q, J=6.8 Hz), 3.64 (1H, d, J=5.6 Hz), 3.59 (1H, octet, J=5.6 Hz), 3.21 (1H, dd, J=7.6, 10.0 Hz), 3.15 (1H, d, J=5.2 Hz), 3.07 (1H, sextet, J=3.6 Hz), 2.90 (3H, s), 2.31 (6H, s), 1.61 (3H, s), 1.33 (3H, d, J=6.8 Hz), 1.28 (3H, d, J=8.0 Hz), 1.23 (3H, d, J=6.4 Hz), 1.23 (3H, s), 1.14 (3H, d, J=7.2 Hz), 0.97 (3H, d, J=7.2 Hz), and 0.88 (3H, t, J=7.6 Hz).

$^{13}$C NMR (100 MHz, $CDCl_3$) δ (attached hydrogens): 205.46 (0), 169.72 (0), 161.01 (0), 102.82 (1), 80.27 (0), 78.46 (0), 77.96 (1), 77.20 (1), 75.21 (1), 70.10 (1), 69.31 (1), 66.10 (1), 66.01 (1), 50.89 (1), 49.69 (3), 46.97 (1), 40.27 (2C, 3), 36.21 (1), 35.90 (2), 30.50 (1), 28.69 (2), 24.27 (3), 22.77 (2), 21.19 (3), 19.94 (3), 19.05 (3), 14.43 (3), 14.23 (3), 13.77 (3), and 10.76 (3).

MS: m/z 612 (M+H).

EXAMPLE 3

9,11-Diamino-9-deoxo-11-deoxy-5-O-desosaminyl-6-O-methyl-3-oxo-9N-((3-quinolin-4-yl)-propyl) erythronolide A, 9N,11N-tetrahydropyrazol 11,12-carbamate (Formula I wherein R is (3-quinolin-4-yl)-propyl and Z is H)

To a solution of 9,11-diamino-9-deoxo-11-deoxy-5-O-desosaminyl-6-O-methyl-3-oxoerythronolide A, 9N,11N-tetrahydropyrazole 11,12-carbamate (18 mg, 0.029 mmol) in Cl(CH$_2$O$_2$Cl (0.5 mL) was added 3-(4-quinolinyl) propionaldehyde (29 mg, 0.156 mmol) HOAc(8 uL, 0.14 mmol) and NaB(OAc)$_3$H (34 mg, 0.16 mmol) and the reaction mixture was stirred at room temperature for 19 h. Sat. NaHCO$_3$ was added, the aqueous layer was extracted with CH$_2$Cl$_2$ (X3), the combined organic layers were washed with brine, dried over anhydrous MgSO$_4$, and concentrated in vaeuo. The crude product was purified by silica gel flash chromatography eluting with 60% acetone-40% hexanes followed by 5% MeOH-1% NH$_3$.H$_2$O-94% CH$_2$Cl$_2$) to afford the title compound as a white solid (16 mg, 53%).

$^1$H NMR (400 MHz, CDCl$_3$) δ: 8.78 (1H, d, J 4.4 Hz), 8.15 (1H, d, J=8.4 Hz), 8.07 (1H, d, J=8.0 Hz), 7.66 (1H, t, J=7.2 Hz), 7.52 (1H, d, J=6.8 Hz), 7.32 (1H, d, J=4.4 Hz), 5.02 (1H, dd, J=3.6, 9.2 Hz), 4.33 (1H, d, J=7.2 Hz), 4.17 (1H, d, J=7.2 Hz), 3.83 (1H, d, J=3.6 Hz), 3.79 (1H, q, J=6.8 Hz), 3.54 (1H, sextet, J=6.0 Hz), 3.31 (1H, 8 peaks, J=7.6 Hz), 3.22 (1H, dd, J=7.2, 10 Hz), 3.16–2.85 (2H, m), 2.79 (3H, s), 2.75–2.55 (2H, m), 2.34 (6H, m), 2.3–1.4 (m), 1.56 (3H, s), 1.32 (3H, d, J=6.8 Hz), 1.25 (3H, d, J=8.4 Hz), 1.23 (3H, d, J=6.4 Hz), 1.20 (3H, s), 1.18 (3H, d, J=8.1 Hz), 0.91 (3H, d, J=7.2 Hz), and 0.88 (3H, d, J=7.2 Hz).

$^{13}$C NMR (100 MHz, CDCl$_3$) δ (attached H's) 204.5 (0), 169.28 (1), 162.79 90), 150.17 (1), 148.82 (0), 148.32 (0), 130.05 (1), 128.89 (1), 127.89 (0), 126.12 (1), 124.01 (1), 121.26 (1), 103.67 (1), 80.06 (1), 79.94 90), 78.88 (0), 78.88 (0), 78.02 (1), 69.32 91), 65.98 (1), 64.49 (1), 51.71 (2), 51.19 (1), 50.52 (3), 46.93 (1), 40.30 (2C, 3), 37.09 (1), 36.24 (2), 29.61 (2), 29.43 (2), 28.87 (2), 26.93 (3), 24.26 (1), 22.64 (2), 21.12 (3), 19.66 (3), 16.64 (3), 14.49 (3), 14.42 (3), 14.09 (3), and 10.77 (3).

MS: m/z 782 (M+H).

The following compounds were prepared by a similar procedure as described above:

9,11-Diamino-9-deoxo-11-deoxy-5-O-desosaminyl-6-O-methyl-3-oxo-9N-(phenylpropyl)erythronolide A, 9N,11N-tetrahydropyrazole, 11,12-carbamate (R is phenylpropyl and Z is H);

9,11-Diamino-9-deoxo-11-deoxy-5-O-desosaminyl-6-O-methyl-3-oxo-9N-((3-pyridin-3-yl-thiazol-4-yl)-propyl)erythronolide A, 9N,11N-tetrahydropyrazole, 11,12-carbamate (R is (3-pyridin-3-yl-thiazol-4-yl)-propyl and Z is H);

9,11-Diamino-9-deoxo-11-deoxy-5-O-desosaminyl-6-O-methyl-3-oxo-9N-(3-(4-phenyl-imidazol-1-yl)-propyl) erythronolide A, 9N,11N-tetrahydropyrazole, 11,12-carbamate (R is 3-(4-phenyl-imidazol-1-yl)-propyl and Z is H);

9,11-Diamino-9-deoxo-11-deoxy-5-O-desosaminyl-6-O-methyl-3-oxo-9N-(3-(2-phenyl-thiazol-5-yl)-propyl) erythronolide A, 9N,11N-tetrahydropyrazole, 11,12-carbamate (R is 3-(2-phenyl-thiazol-5-yl)-propyl and Z is H); and 9,11-Diamino-9-deoxo-11-deoxy-5-O-desosaminyl-6-O-methyl-3-oxo-9N-(3-(4-phenyl-1H-imidazol-2-yl)-propyl)erythronolide A, 9N,11N-tetrahydropyrazole, 11,12-carbamate (R is 3-(4-phenyl-1H-imidazol-2-yl)-propyl and Z is H).

What is claimed is:

1. A compound of the formula:

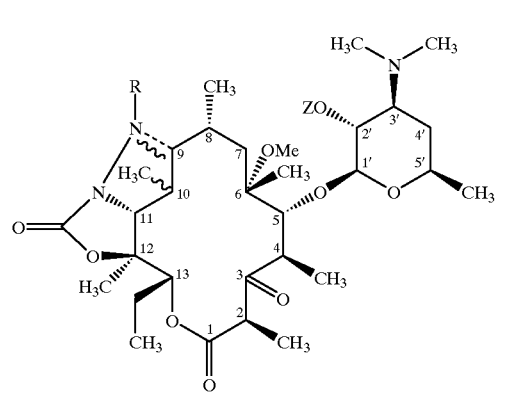

or a pharmaceutically acceptable salt thereof, wherein:

R is H, R$^1$, C(═O) R$^1$, C(═O) OR$^1$, (CH$_2$)$_m$R$^3$, or is absent, wherein m is an integer from 0 to 6;

R$^3$ is a 5–10 membered heterocycle or C$_6$–C$_{10}$ aryl, wherein said heterocyclic and aryl groups are optionally substituted by 1 to 3 substituents independently selected from the group consisting of —C(O)OR$^4$, —OR$^4$, C$_1$–C$_6$ aklanoyl, halo, nitro, cyano, C$_1$–C$_6$ alkyl, —NR$^4$R$^5$, —S(C$_1$–C$_6$ alkyl), —SO(C$_1$–C$_6$ alkyl), —SO$_2$(C$_1$–C$_6$ alkyl) and —SO$_2$NR$^4$R$^5$;

each R$^4$ and R$^5$ is independently the group consisting of H and C$_1$–C$_{10}$ alkyl, saturated or unsaturated, wherein one or two carbons of said alkyl are optionally replaced by a heteroatom selected from O, S and N;

R$_1$ is selected from the group consisting of saturated C$_1$–C$_{10}$ alkyl and unsaturated C$_1$–C$_{10}$ alkyl, wherein one or two carbons of said alkyl are optionally replaced by a heteroatom selected from O, S and N, and are optionally substituted by 1 to 3 substituents selected from the group consisting of —C(O)OR$^4$, —OR$^4$, C$_1$–C$_6$ alkanoyl, halo, nitro, cyano, C$_1$–C$_6$ alkyl, 5–10 membered hetercycle, C$_6$–C$_{10}$ aryl, —NR$^4$R$^5$, —S(C$_1$–C$_6$ alkyl), —SO(C$_1$–C$_6$ alkyl), —SO$_2$(C$_6$ alkyl) and —SO$_2$NR$^4$R$^5$; and Z is H, C(═O)R$^4$ or C(═O)R$^3$, wherein R$^4$ is defined as above.

2. The compound of claim 1 wherein Z is H.

3. The compound of claim 1 wherein R is absent.

4. The compound of claim 1 wherein R is H.

5. The compound of claim 1 wherein R is (CH$_2$)$_m$ R$^3$ wherein m is an integer ranging from 0 to 6 and R$^3$ is 5–10 membered heterocycle or C$_6$–C$_{10}$ aryl.

6. The compound of claim 5 wherein R$^3$ is selected from the group consisting of: quinolin-4-yl, 4-phenyl-imidazol-1-yl, imidazo(4,5-b)pyridin-3-yl, 4-pyridin-3-yl-imidazol-1-yl and pyridin-3-yl.

7. The compound of claim 1 wherein said compound is selected from the group consisting of:

11-Amino-9-deoxo-11-deoxy-5-O-desosaminyl-9-imino-6-O-methyl-3-oxoerythronolide A, 9N,11N-dihydropyrazole, 11,12-carbamate;

9,11-Diamino-9-deoxo-11-deoxy-5-O-desosaminyl-6-O-methyl-3-oxoerythronolide A, 9N,11N-tetradropyrazole, 11,12-carbamate;

9,11-Diamino-9-Deoxo-11-deoxy-5-O-desosaminyl-6-O-methyl-3-oxo-9N-((3-quinolin-4-yl)-propyl) erythronolide A, 9N,11N-tetrahydropyrazole, 11,12-carbamate, 9,11-Diamino-9-deoxo-11-deoxy-5O-desosaminyl-6-O-methyl-3-oxo-9N-(phenylpropyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-pyridin-3-yl-thiazol-4-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-phenyl-imidazol-1-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-pyridin-3-yl-imidazol-1-yl)-propyl)erythronolide A, 9N,11N-tetrahydropyrazole, 11,12-carbamate;

9,11-Diamino-9-dexo-11-deoxy-5-O-desosaminyl-6-O-methyl-3-oxo-9N-(3-(imidazo(4,5-b)pyridin-3-yl)-propyl)erythronolide A, 9N,11N-tetrahydropyrazole, 11,12-carbamate;

9,11-Diamino-9-11-deoxy-5-O-desosaminyl-6-O-methyl-3-oxo-9N-(3-(pyridin-3-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(2-phenyl-thiazol-5-yl)-propyl)erythronolide A, 9N,11N-tetrahydropyrazole, 11,12-carbamate;

9,11-Diamino-9-deoxo-11-deoxy-5-O-desasaminyl-6-O-methyl-3-oxo-9N-(3-(4-phenyl-1H-imidazol-2-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-quinolin-4-yl)-propionyl)erythronolide erythronolide A, 9N,11N-tetrahydropyrazole, 11,12-carbamate;

9,11-Diamino-9-deoxo-11-deoxy-5-O-desosaminyl-6-O-methyl-3-oxo-9N-((phenyl)-propionyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-((3-pyridin-3-yl-thiazol-4-yl)-propyl)erythronolide A, 9N,11N-tetrahydropyrazole, 11,12-carbamate;

9,11-Diamino-9-deoxo-11-deoxy-5-O-desosaminyl-6-O-methyl-3-oxo-9N(3-(4-phenyl-imidazol-1-yl)-propionyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(2-phenyl-thiazol-5-yl)-propionyl)erythronolide A, 9N,11N-tetrahydropyrazole, 11,12-carbamate;

9,11-Diamino-9-deoxo-11-deoxy-5-O-desosaminyl-6-O-methyl-3-oxo-9N-(3-(4-phenyl-1H-imidazol-2-yl)-propionyl)erythronolide A, 9N,11N-tetrahydropyrazole, 11,12-carbamate; and the pharmaceutically acceptable salts of said compounds.

8. A pharmaceutical composition for the treatment of a bacterial infection or protozoa infection in a mammal, fish or bird which comprises a therapeutically effective amount of a compound of claim 1 and a pharmaceutically acceptable carrier.

9. A method of treating a bacterial infection or protozoa infection in a mammal, fish, or bird which comprises administering to said mammal, fish, or bird a therapeutically effective amount of a compound of formula 1, or a pharmaceutically acceptable salt thereof, as defined in claim 1.

10. A method of preparing a compound of the formula:

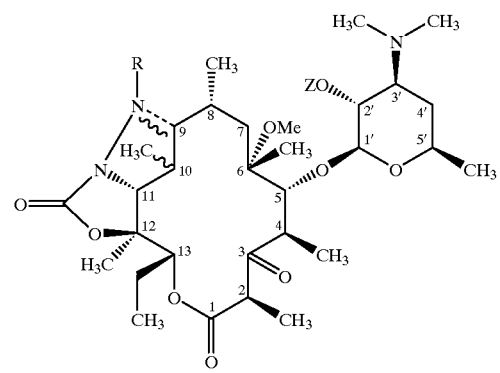

or a pharmaceutically acceptable salt thereof, wherein
R is H, $R^1$, $C(=O) R^1$, $C(=O) OR^1$, $(CH_2)_m R^3$, or is absent, wherein m is an integer from 0 to 6;

$R^3$ is a 5–10 membered heterocycyl or $C_6$–$C_{10}$ aryl, wherein said heterocyclic and aryl groups are optionally substituted by 1 to 3 substituents independently selected from the group consisting of —$C(O)OR^4$, —$OR^4$, $C_1$–$C_6$ alkanoyl, halo, nitro, cyano, $C_1$–$C_6$ alkyl, —$NR^4R^5$, —$S(C_1$–$C_6$ alkyl), —$SO(C_1$–$C_6$ alkyl), —$SO_2(C_1$–$C_6$ alkyl) and —$SO_2NR^4R^5$;

each $R^4$ and $R^5$ is independently selected from the group consisting of H and $C_1$–$C_{10}$ alkyl, saturated or unsaturated, wherein one or two carbons of said alkyl are optionally replaced by a heteroatom selected from O, S and N;

$R^1$ is selected from the group consisting of saturated $C_1$–$C_{10}$ alkyl and unsaturated $C_1$–$C_{10}$ alkyl, wherein one or two carbons of said alkyl are optionally replaced by a heteroatom selected from O, S and N, and are optionally substituted by 1 to 3 substituents selected from the group consisting of —$C(O)OR^4$, $C_1$–$C_6$ alkanoyl, halo, nitro, cyano, $C_1$–$C_6$ alkyl, 5–10 membered heterocycyl, $C_6$–$C_{10}$ aryl, —$NR^4R^5$, —$S(C_1$–$C_6$ alkyl), —$SO(C_1$–$C_6$ alkyl), —$SO_2(C_1$–$C_6$ alkyl) and —$SO_2NR^4R^5$; and Z is H or $C(=O)R^4$, wherein $R^4$ is defined as above, which comprises: treating a compound of the formula:

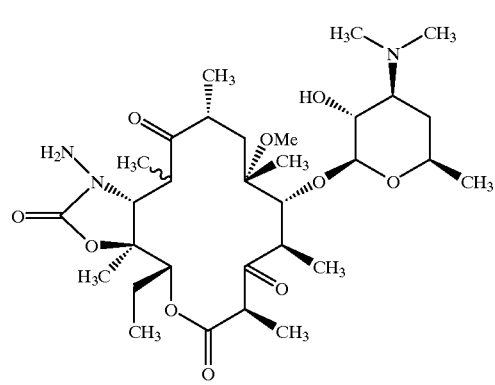

with an acid in the presence of a protic solvent to form the compound of formula I.

11. The method of claim 10 wherein said solvent is methanol, ethanol, or isopropyl alcohol.

12. The method of claim 10 wherein said acid is p-toluenesulfonic acid or pyridinium p-toluenesultonate.

* * * * *